United States Patent [19]

Kurichev et al.

[11] 4,165,740

[45] Aug. 28, 1979

[54] MEDICAL ALTITUDE CHAMBER

[75] Inventors: Viktor I. Kurichev; Boris V. Spolitak, both of Moscow, U.S.S.R.

[73] Assignee: Vsesojuzny Nauchno-Issledovalelsky Ispytatelny Institut Meditsinskoi Tekhniki, U.S.S.R.

[21] Appl. No.: 828,850

[22] Filed: Aug. 29, 1977

[51] Int. Cl.[2] .......... A61M 16/02

[52] U.S. Cl. .......... 128/204; 128/1 B; 137/209; 137/88; 137/98

[58] Field of Search .......... 128/204, 1 B, 191 A; 98/1.5; 137/209, 88, 98

[56] References Cited

U.S. PATENT DOCUMENTS

| | | | |
|---|---|---|---|
| 3,593,738 | 7/1971 | Baerfuss | 137/209 |
| 3,877,427 | 4/1975 | Alexeev et al. | 128/204 |

FOREIGN PATENT DOCUMENTS

| | | | |
|---|---|---|---|
| 382416 | 8/1973 | U.S.S.R. | 128/204 |
| 534240 | 1/1977 | U.S.S.R. | 128/204 |

*Primary Examiner*—Henry J. Recla
*Attorney, Agent, or Firm*—Steinberg and Blake

[57] ABSTRACT

The medical altitude chamber is constituted by a pressuretight therapeutic chamber communicating with a source of a gas medium under pressure. It also incorporates apparatus for moistening the gas medium in the therapeutic chamber, said apparatus comprising a liquid reservoir whose lower part communicates through an adjustable throttle with the internal space of the jet pump nozzle, and a pressure regulator which has an inlet for communication with the source of the gas medium, a setting inlet for communication with the therapeutic chamber, and an outlet for communication with the upper part of the liquid reservoir.

2 Claims, 1 Drawing Figure

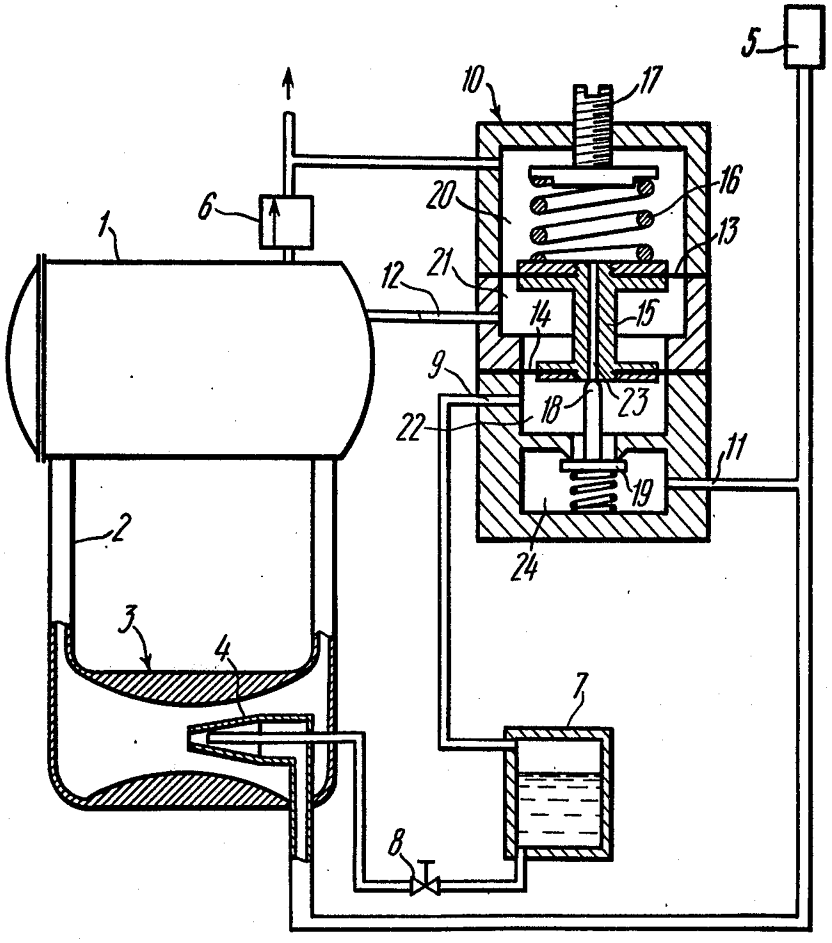
1
2
3
4
5
6
7
8
9
10
11
12
13
14
15
16
17
18
19
20
21
22
23
24

MEDICAL ALTITUDE CHAMBER

The present invention relates to medical engineering and more specifically it relates to altitude chambers intended for medical treatment with oxygen or mixtures thereof.

Known in the prior art is a medical altitude chamber manufactured by "Vickers" and designed for medical treatment with oxygen.

The prior art altitude chamber is a pressuretight therapeutic chamber intended to accommodate a patient, and communicating with a pipe which incorporates a built-in jet pump whoze nozzle is adapted to put be in fluid communication with a source of a gas under pressure, i.e. oxygen. The therapeutic chamber is provided with valves for the discharge of oxygen and may have a provision for recirculation of the gas medium. For this purpose the jet pump is built into a pipe which, together with the therapeutic chamber, forms a recirculating circuit. This circuit may comprise also a cooling heat exchanger. The source of gas supply in the prior art altitude chamber is constituted, as a rule, By H.P. bottles with dry oxygen. The source of moisture for moistening the gas medium in the known altitude chambers is provided by the patient himself.

The humidity control in the medical altitude chambers is of great importance both from the medical and technical points of view. The predetermined humidity should be maintained for normal functioning of the physiologic thermoregulation of a living organism in order, for preventing irreversible changes in epithelial tissues and, finally, for retaining the humidity balance of said organism.

From the technical point of view, the maintenance of a predetermined humidity gives protection against accumulation of an electrostatic charge on the dielectric surfaces inside the therapeutic chamber and reduces the fire hazard that may be caused by an electric discharge.

In the prior art altitude chamber the humidity control is effected by setting the "dew point" in the cooling heat exchanger and by condensation of surplus moisture in the gas circulation circuit. Thus, humidity regulation is impossible unless the patient exhudes sufficient amount of moisture which is accumulated in ample quantities in the therapeutic chamber. However, exudation of moisture by the patient may be quite insignificant. It means, that when the air is being substituted in the therapeutic chamber by oxygen or another medium and during the substantial part of the treating session the level of humidity in the therapeutic chamber may be considerably lower than required. In the altitude chamber without circulation of the gas medium the humidity cannot be regulated because a considerable portion of moisture exhuded by the patient is carried away from the chamber.

An object of the invention is to ensure regulation of moistening of the gas medium in the altitude chamber at all operating modes and in accordance with the pressure prescribed for a certain curative treatment.

The essence of the invention resides in providing a medical altitude chamber which consists of a pressure-tight therapeutic chamber communicating through a pipe with a jet pump incorporated therein, the jet pump nozzle being adapted to put the pump in communication with a source of a gas medium under pressure and which has at least one valve for discharging the gas medium from the therapeutic chamber wherein, according to the invention a means is provided for moistening the gas medium in the therapeutic chamber, said means being essentially a reservoir for liquid whose lower part communicates via an adjustable throttle with the internal space of the jet pump nozzle whereas the upper part is in communication with the outlet of a pressure regulator which has a setting inlet communicating with the therapeutic chamber and an inlet intended for communication with the source of the gas medium.

In the medical altitude chamber according to the invention the supply of liquid into the nozzle of the jet pump allows the high-velocity flow of fresh gas medium to be utilized for intensive atomization of the supplied liquid. Further atomization and evaporation of the supplied liquid takes place in the mixing chamber of the jet pump.

The introduction of a pressure regulator into the liquid supply system provides for automating the correction of liquid supply at pressure changes in the therapeutic chamber.

A combination of efficient evaporation with accurate metering of the supplied liquid ensures adequate regulation of humidity of the gas medium in the medical altitude chamber.

Now the invention will be described in detail by way of example with reference to the accompanying drawing which illustrates the medical altitude chamber according to the invention with a partial longitudinal section.

The medical altitude chamber comprises a pressure-tight therapeutic chamber 1, a pipe 2 provided with a built-in jet pump 3 having a nozzle 4 for the delivery of a gas medium from a source 5 of gas medium under pressure, said source being constituted by, say, a bottle with compressed gas, and a valve 6 for discharging the gas medium and maintaining the required pressure in the therapeutic chamber 1. In addition, the medical altitude chamber has a means for moistening the gas medium in the therapeutic chamber 1 consisting of a liquid reservoir 7 whose lower part communicates via an adjustable throttle 8 with the internal space of the nozzle 4 of the jet pump 3 while the upper part communicates with the outlet 9 of a pressure regulator 10 whose inlet 11 is adapted to provide communication with the source 5 of a gas medium under pressure whereas the setting inlet 12 of said pressure regulator 10 is in communication with the therapeutic chamber 1.

In this embodiment of the invention the required relative humidity is set by the adjustable throttle 8 while the pressure regulator 10 introduces corrections into the consumption of water for moistening the gas medium at changes of pressure in the therapeutic chamber 1.

The described embodiment of the invention utilizes a simple double-membrane pressure regulator specially designed for operation with a certain therapeutic chamber. The regulator 10 comprises a housing which is located two membranes 13 and 14 having different effective areas, the effective area of the membrane 13 being larger. Membranes 13 and 14 define within the housing three spaces, namely, a first upper space 20 defined by the housing and the membrane 13, a second, intermembrane space 21 defined by the housing and the two membranes 13, 14 and a third, lower space 22 defined by the housing and membrane 14. The membranes 13 and 14 are rigidly linked with each other by a connector 15. The membrane unit 13 and 14 is acted upon by a spring 16 whose tension is adjusted by a screw 17. The membrane unit 13, 14 is connected with a valve 19 via a pusher 18. The above-membrane space 20 of the regulator 10 is in communication with the atmosphere. The inter-membrane space 21 communicates with the setting inlet 12. The under-membrane space 22 communicates with the outlet 9 of the regulator 10. Besides, the connector 15 is provided with a channel 23 closed with the pusher 18 for communicating the under-membrane space 22 with the atmospheric outlet. A fourth space 24 is supplied with a gas medium under pressure from the source 5 of the gas medium through the inlet 11 of the regulator 10.

The medical altitude chamber according to the invention functions as follows.

In order to ensure the preset humidity in the therapeutic chamber 1 at a constant rate of flow of a fresh gas medium, the amount of moisture supplied into the therapeutic chamber 1 should be inversely proportional to the pressure in said chamber.

During scavenging of the therapeutic chamber 1 (substitution of the gas medium in the therapeutic chamber) at a pressure of about $10^5$ Pa the moistening means supplies the moistening liquid to ensure the preset humidity which is set by moving the handle of the adjustable throttle 8.

The pressure regulator 10 builds up a maximum pressure in the upper part of the liquid reservoir 7 in order to create a maximum pressure drop on the adjustable regulator 8.

The pressure at the edge of the pipe connecting the nozzle 4 with the throttle 8 is practically constant at all the operating modes of the therapeutic chamber 1 because it depends on the pressure built up by the source 5 of the gas medium and on the velocity of the flow in the nozzle 4 of the jet pump 3.

In the described embodiment of the invention the pressure drop in the nozzle 4 is selected to be above-critical for simplicity of discussion, therefore the velocity of the flow is constant at all the operating modes of the therapeutic chamber 1.

In the compression mode the pressure in the therapeutic chamber 1 rises and the setting inlet 12 of the pressure regulator 10 is subjected to a higher pressure. Due to the difference of the effective areas of the membranes 13 and 14 the pressure at the setting inlet 12 creates a force which is directed against the action of the spring 16 and compensates partly for the force of the spring 16. As a result, the valve 19 closes to some extent and the pressure at the outlet 9 of the pressure regulator 10 decreases. This is accompanied by a simultaneous reduction of pressure in the upper part of the liquid reservoir 7 through channel 23 to atmosphere and of the pressure difference on the adjustable throttle 8.

This, in turn, decreases the supply of the moistening liquid and retains the preset relative humidity at any pressure in the therapeutic chamber 1.

In the ventilation mode at a steady pressure in the therapeutic chamber 1 the pressure difference on the throttle 8 remains constant and the therapeutic chamber 1 is supplied with a constant amount of moisture required for ensuring the preset humidity.

In the decompression mode (reduction of pressure), the process is contrary to that taking place in the compression mode: a pressure drop in the therapeutic chamber 1 is accompanied by a pressure rise at the outlet 9 of the pressure regulator 10 and, accordingly, in the upper part of the liquid reservoir 7, and by an increased supply of moisture into the therapeutic chamber 1.

Thus, in all the operating modes of the therapeutic chamber 1 there is a constant relative humidity of the gas medium in the medical altitude chamber.

What is claimed is:

1. A medical altitude compression chamber apparatus comprising: a pressure tight therapeutic chamber adapted to contain a gas under pressure; a jet pump; first pipe means for providing fluid communication between said jet pump and said therapeutic chamber; said jet pump being at least partially defined by a nozzle having an inlet and an outlet; second pipe means for providing fluid communication between the nozzle inlet and a source of pressurized gas; at least one valve means for discharging gas from said therapeutic chamber; means responsive to the pressure of the gas contained in said pressure tight chamber for moistening the gas therein, said moistening means including a liquid reservoir having liquid and gas containing portions, third pipe means for providing fluid communication between the said liquid containing portion of said reservoir and an internal space defined within said nozzle, adjustable throttle means interposed in said third pipe means for adjustably controlling the flow of liquid from said liquid reservoir to said nozzle, and pressure regulator means fluidly communicating with said chamber and liquid reservoir and adapted to communicate with a source of pressurized gas for adjusting the pressure of the liquid in said liquid reservoir in response to changes in the pressure of the gas contained in said pressure tight chamber in a manner such that upon the pressure of the gas in the pressure tight chamber increasing, the pressure of the liquid in the liquid reservoir decreases, and upon the pressure of the gas in the pressure tight chamber decreasing, the pressure of the liquid in the liquid reservoir increases, whereby the flow of liquid to the nozzle from the liquid reservoir through the third pipe means varies inversely with the change in the gas pressure within the chamber.

2. A chamber apparatus as recited in claim 1 wherein said pressure regulator means comprises a housing; first and second membranes substantially parallely disposed to each other in said housing, said first membrane having a larger effective surface area than said said second membrane, said first membrane and housing defining a first space, said first and second membranes defining a second space and said third membrane and housing defining a third space; a connector element rigidly interconnecting said first and second membranes, said connector element having a passage formed therethrough providing fluid communication between said first and third spaces, a fourth space defined within said housing; aperture means for providing fluid communication between said third and fourth spaces; valve means located in said aperture means for adjusting the extent of fluid communication between said third and fourth spaces, pusher means associated with said valve means extending between said valve means and connector element, spring means located in said first space normally urging said connector element into engagement with said pusher means; said second pipe means fluidly interconnecting said nozzle and said fourth space, and further including fourth pipe means fluidly interconnecting said third space and said gas containing portion of the liquid reservoir, fifth pipe means fluidly interconnecting said chamber and said second space; sixth pipe means for providing fluid communication between said fourth space and a source of pressurized gas, and means for providing fluid communication between said first space and the atmosphere.

* * * * *